(12) United States Patent
Swain

(10) Patent No.: US 11,298,712 B2
(45) Date of Patent: Apr. 12, 2022

(54) PERSONAL DISPENSER

(71) Applicant: Renee Swain, Westland, MI (US)

(72) Inventor: Renee Swain, Westland, MI (US)

( * ) Notice: Subject to any disclaimer, the term of this patent is extended or adjusted under 35 U.S.C. 154(b) by 0 days.

(21) Appl. No.: 16/828,881

(22) Filed: Mar. 24, 2020

(65) Prior Publication Data
US 2021/0299689 A1  Sep. 30, 2021

(51) Int. Cl.
*B05B 11/00* (2006.01)
*B05B 15/60* (2018.01)
*A47K 5/12* (2006.01)
*A61L 2/00* (2006.01)

(52) U.S. Cl.
CPC ........ *B05B 11/3032* (2013.01); *A47K 5/1201* (2013.01); *A47K 5/1208* (2013.01); *A61L 2/0088* (2013.01); *B05B 11/3073* (2013.01); *B05B 15/60* (2018.02); *A61L 2202/15* (2013.01); *A61L 2202/16* (2013.01)

(58) Field of Classification Search
CPC . B05B 11/3032; B05B 15/60; B05B 11/3073; A47K 5/1201; A47K 5/1208; A61L 2202/15; A61L 2202/16
USPC ........................................................ 222/175
See application file for complete search history.

(56) References Cited

U.S. PATENT DOCUMENTS

| | | | | |
|---|---|---|---|---|
| 4,058,237 A | * | 11/1977 | Luke .......................... | F41H 9/10 222/78 |
| 5,503,304 A | * | 4/1996 | Keller ....................... | F41H 9/10 222/175 |
| 5,924,601 A | * | 7/1999 | Chen ......................... | F41H 9/10 222/175 |
| 6,123,228 A | * | 9/2000 | Hippensteel ......... | A44C 9/0053 222/153.11 |
| 2002/0170927 A1 | * | 11/2002 | Gerstner ................... | F41H 9/10 222/175 |
| 2015/0158042 A1 | * | 6/2015 | Parker ....................... | A61L 2/18 222/175 |
| 2016/0044997 A1 | * | 2/2016 | Horgan ..................... | A45F 5/00 222/175 |
| 2020/0245822 A1 | * | 8/2020 | Chacon, Jr. .......... | A44C 5/0007 |

* cited by examiner

*Primary Examiner* — Jeremy Carroll
(74) *Attorney, Agent, or Firm* — Heed Law Group; Thomas P. Heed

(57) ABSTRACT

A wearable dispenser with a replaceable one-time-use reservoir device is taught, comprising a wrist-band allowing the wearable dispenser to be worn by a user; a base connected to the wrist-band; and a replaceable one-time-use reservoir. The replaceable one-time-use reservoir is comprised of a flexible bladder holding a substance to be dispensed, a housing with a rigid perimeter wall, a flexible top surface attached to the rigid perimeter wall and covering the flexible bladder, a one-way valve, an opening, and a substance to be dispensed. Typically, the substance to be dispensed is hand sanitizer. A user may use their fingertip to press the flexible top surface. Doing so creates additional pressure within the flexible bladder, causing the substance to be dispensed.

16 Claims, 8 Drawing Sheets

PERSONAL DISPENSER

FIELD OF INVENTION

This invention relates to the classifications for human necessities and performing operations; and to one or more sub-classifications relating to hand or travelling articles; or to conveying, packing, storing, and handling. Specifically, this invention is a wearable dispenser with a replaceable one-time-use reservoir containing hand sanitizer.

BACKGROUND OF INVENTION

The emergence of the corona virus has shown the importance of good hand hygiene. People are being told to avoid crowds, avoid touching surfaces in public places, and wash their hands often. The reality is that for many people, avoiding crowds, not touching surfaces in public places, and/or immediately washing their hands after doing so, is an impossibility.

Children are exposed to large crowds on a repeated basis at schools and daycares worldwide. As every parent of school-age children knows, these institutions are veritable incubators of viruses. Children in a school or daycare share lunch tables, desks, chairs, work-stations, and other surfaces. They all touch the same door knobs, doors, water fountains, and spigots. It is impossible for children to wash their hands as often as they touch potentially contaminated surfaces. Children get sick all the time at school and daycares.

Likewise, adults are exposed to the same risks in work environments, airports, and hotels. No matter how well-intentioned an individual is, it is nearly impossible to be scrupulous with hand-washing in public.

Therefore, a need exists to provide individuals with a ready solution to hand hygiene. The solution taught in this application is a personal, wearable dispenser with a replaceable, one-time-use reservoir of hand-sanitizer. The invention taught in this application overcomes the problems with the prior art as discussed above, and particularly provides a portable and wearable dispenser of hand sanitizer.

SUMMARY OF THE INVENTION

This summary is intended to disclose a wearable dispenser with a replaceable, one-time-use reservoir. This summary is not intended to limit the claimed subject matter's scope. Rather, it is intended to provide one skilled in the art with an overview of the invention by referencing its main embodiments. The invention taught extends beyond the simplified concepts taught in this summary.

A wearable dispenser with a replaceable one-time-use reservoir device is disclosed. It comprises a wrist-band allowing the wearable dispenser to be worn by a user; a base connected to the wrist-band; and a replaceable one-time-use reservoir. The replaceable one-time-use reservoir is comprised of a flexible bladder holding a substance to be dispensed, a housing with a rigid perimeter wall, a flexible top surface attached to the rigid perimeter wall and covering the flexible bladder, a one-way valve, an opening, and a substance to be dispensed. Typically, the substance to be dispensed is hand sanitizer. The replaceable one-time-use reservoir is attached to the base.

The interior of the flexible bladder is evacuated prior to filling. When the replaceable one-time-use reservoir is new, the flexible bladder is filled with a substance to be dispensed, such as hand sanitizer. The pressure within the flexible bladder is greater than atmospheric pressure.

The one-way valve is comprised of a plunger, a spring, a stem, and a stop. The stem is hollow, creating a dispensing channel. The plunger of the valve is inside the flexible bladder. When the flexible top surface is not pressed, the one-way valve is in equilibrium. In equilibrium, the spring force of the spring is more than the force created by the pressure on the plunger. In equilibrium, the one-way valve is closed. In equilibrium, the stop prevents any of the substance from flowing through the dispensing channel.

A user may use their fingertip to press the flexible top surface. Doing so creates additional pressure within the flexible bladder. The combined pressure on the plunger within the flexible bladder is sufficient to compress the springs. Once the springs are compressed, the one-way valve allows some of the substance within the flexible bladder to be dispensed through the opening. When all of the substance within the flexible bladder has been dispensed, the replaceable one-time-use reservoir may be removed and replaced with a new replaceable one-time-use reservoir.

The flexible bladder is fabricated from an elastic material such as natural rubber, nitrile rubber, butyl rubber, elastomers, or thermoplastic elastomers. The flexible bladder is most appropriately constructed from a synthetic rubber, such as polychloroprene, ethylene-propylene-diene-modified ("EPDM"), styrene-butadiene rubbers ("SBR"), polyisoprene, and acrylonitrile butadiene rubber ("ABR"), inter alia. The housing, rigid perimeter wall, and base are each constructed from at least one of steel, zinc, aluminum, acrylonitrile butadience styrene ("ABS"), polycarbonate ("PC"), polypropylene ("PP"), polyamides ("nylon"), polyethylene ("PE"), and polyvinyl chloride ("PVC").

BRIEF DESCRIPTION OF THE DRAWINGS

The present invention is illustrated with 6 drawings on 8 sheets. The accompanying drawings, which are incorporated in and constitute a part of this disclosure, illustrate various example embodiments. In the drawings.

DETAILED DESCRIPTION OF THE DRAWINGS

Figure 1:
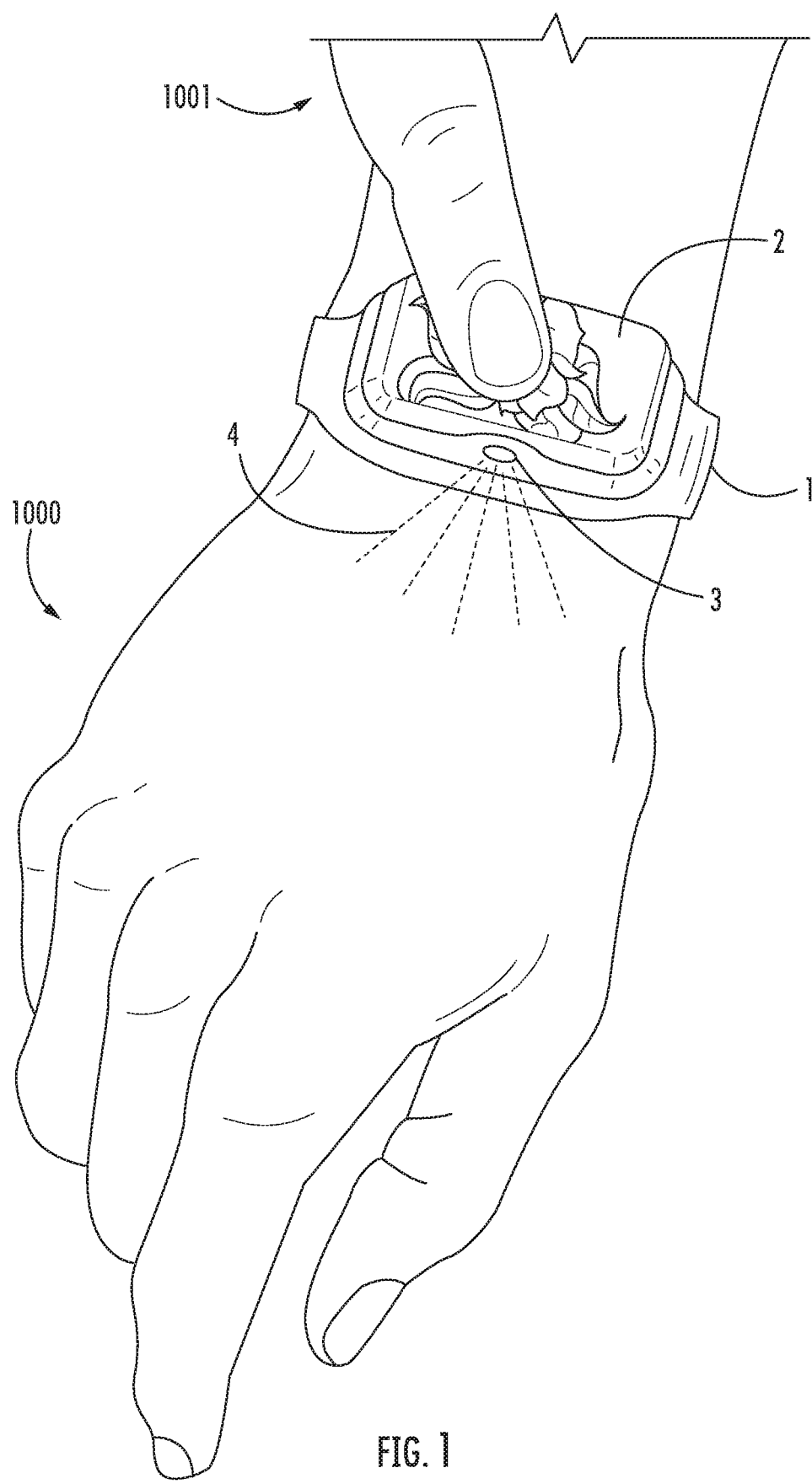
FIG. 1 depicts an in situ, perspective view of an example embodiment of the present invention, a wearable dispenser with a replaceable one-time-use reservoir.

The following descriptions are not meant to limit the invention, but rather to add to the summary of invention, and illustrate the present invention, a wearable dispenser with a replaceable one-time-use reservoir. The present invention is illustrated with a variety of drawings showing the primary embodiments of the present invention, with various diagrams and figures explaining its workings.

Certain terminology is used in the following description for convenience only and is not limiting. The article "a" is intended to include one or more items, and where only one item is intended the term "one" or similar language is used. To assist in the description of the present invention, words such as short, long, top, bottom, side, upper, lower, front, rear, inner, outer, right and left are used to describe the relative size and orientation of the present invention with respect to the cellphone in the accompanying figures. The terminology includes the words above specifically mentioned, derivatives thereof, and words of similar import.

The following detailed description refers to the accompanying drawings. Wherever possible, the same reference numbers are used in the drawings and the following description to refer to the same or similar elements. While embodiments of the claimed subject matter may be described, modifications, adaptations, and other implementations are possible. For example, substitutions, additions, or modifications, which perform identical functions to the embodiments disclosed, may be made to the elements illustrated in the drawings. Accordingly, the following detailed description does not limit the claimed subject matter. The proper scope of the claimed subject matter is defined by the claims contained herein.

The claimed subject matter improves over the prior art by providing a wearable dispenser with a replaceable one-time-use reservoir. The claimed subject matter presents an inexpensive wearable dispenser with a replaceable one-time-use reservoir that allows a user to have ready access to a substance to be dispensed, such as hand sanitizer.

FIG. 1 shows the present invention, a wearable dispenser with a replaceable one-time-use reservoir 1, in situ, on the wrist of a user 1000. By using a fingertip 1001 to depress the flexible top surface 2, the user 1000 can dispense a substance 4, such as hand-sanitizer, through a one-way valve 3.

Figure 2:
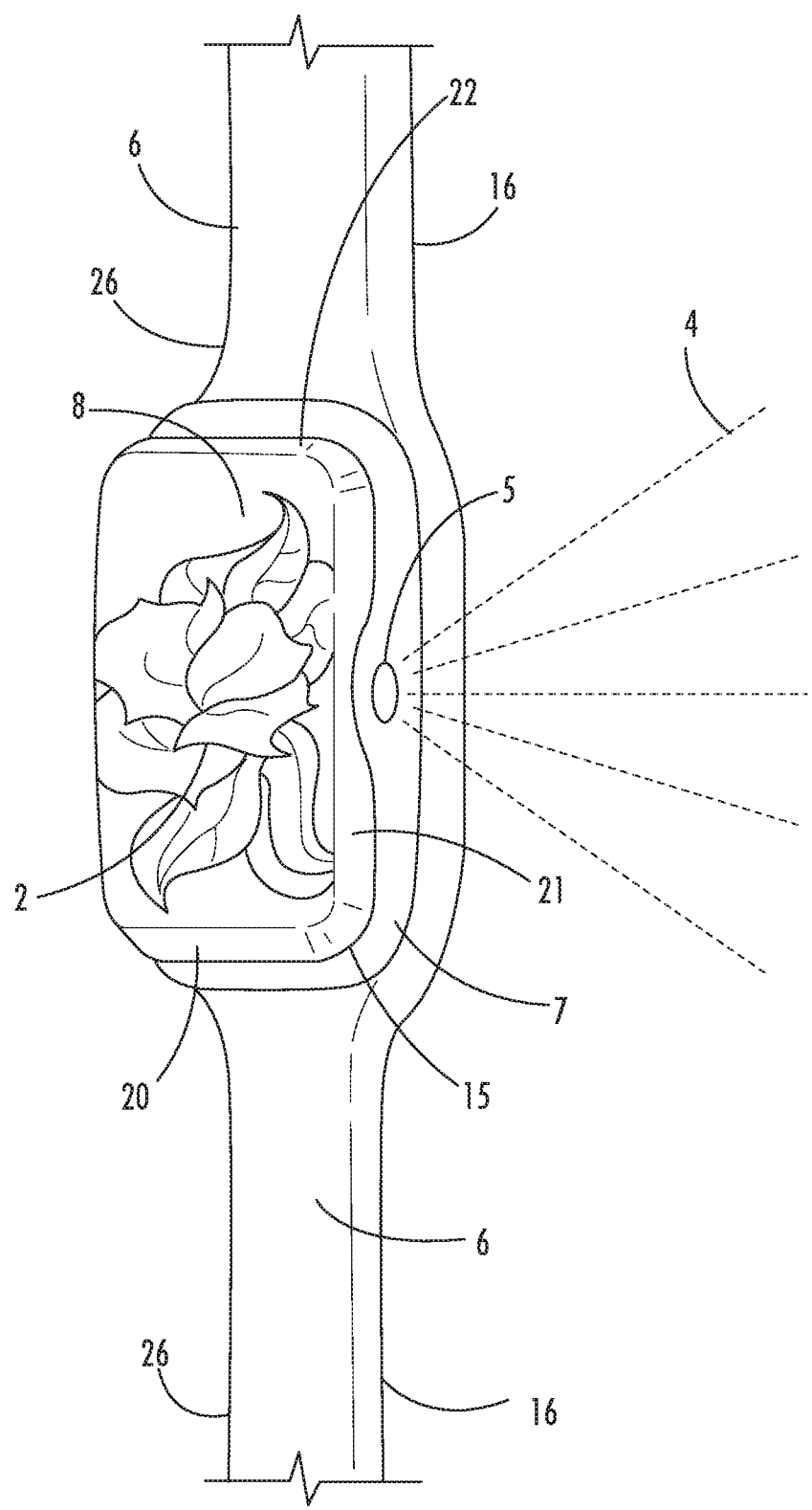
FIGS. 2 and 3 depict perspective isolation views of alternative embodiments of the present invention, a wearable dispenser with a replaceable one-time-use reservoir.

FIG. 2 shows the present invention, a wearable dispenser with a replaceable one-time-use reservoir, in isolation. The flexible top surface 2 covers the replaceable one-time-use reservoir 8. When the flexible top surface 2 is depressed, it creates pressure within the replaceable one-time-use reservoir 8, causing it to dispense a substance 4 from an opening 5. The replaceable one-time-use reservoir 8 has a top surface 2, a first long side surface 21, a first short side surface 22, a second short side surface 20, and a second long side surface (obscured in this view). The first long side surface 21 is contoured. The replaceable one-time-use reservoir 8 mates with a base 7 at a mating line 15. The wearable dispenser with a replaceable one-time-use reservoir 1 has a wrist-band 6 with a top surface 6, a left side 26, and a right side 16 so that it may be worn by a user 1000. The wrist-band 6 may be continuous and elastic, so that it may be stretched to fit onto the wrist of the user 1000. The wrist-band 6 may have common connectors such as clasps to facilitate being fitted onto the user's 1000 wrist. The wrist-band 6 may have two ends which can be connected, like a wrist-watch band.

Figure 3:
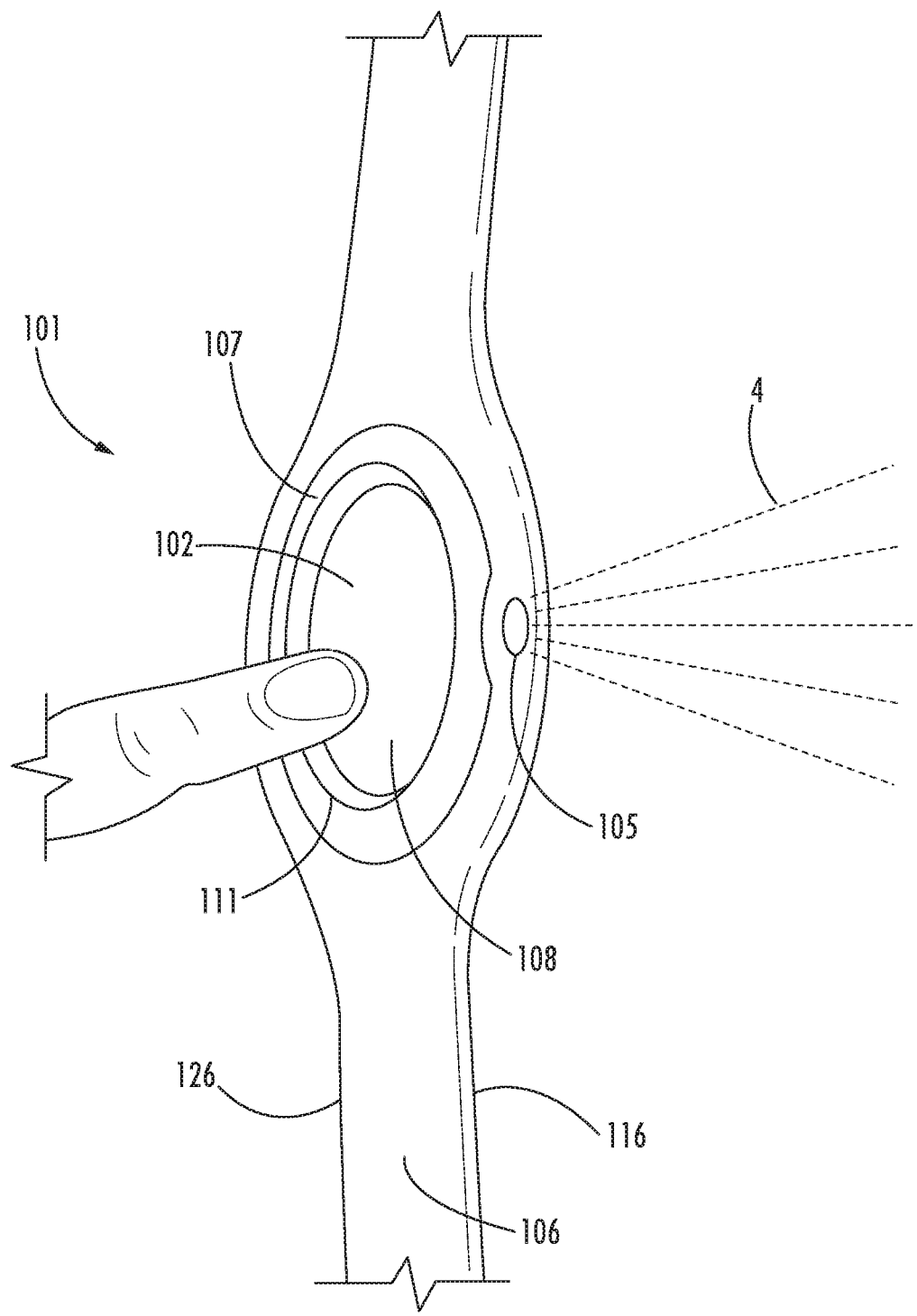

FIG. 3 shows an alternative embodiment of the present invention 101, a wearable dispenser with a replaceable one-time-use reservoir, in isolation. The flexible top surface 102 covers the replaceable one-time-use reservoir 108. When the flexible top surface 102 is depressed, it creates pressure within the replaceable one-time-use reservoir 108, causing it to dispense a substance 4 from an opening 105. The replaceable one-time-use reservoir 108 sits within the inner diameter 111 of the base 107. The wearable dispenser with a replaceable one-time-use reservoir 101 has a wrist-band 106 with a top surface 106, a left side 126, and a right side 116 so that it may be worn by a user 1000.

Figure 4A:
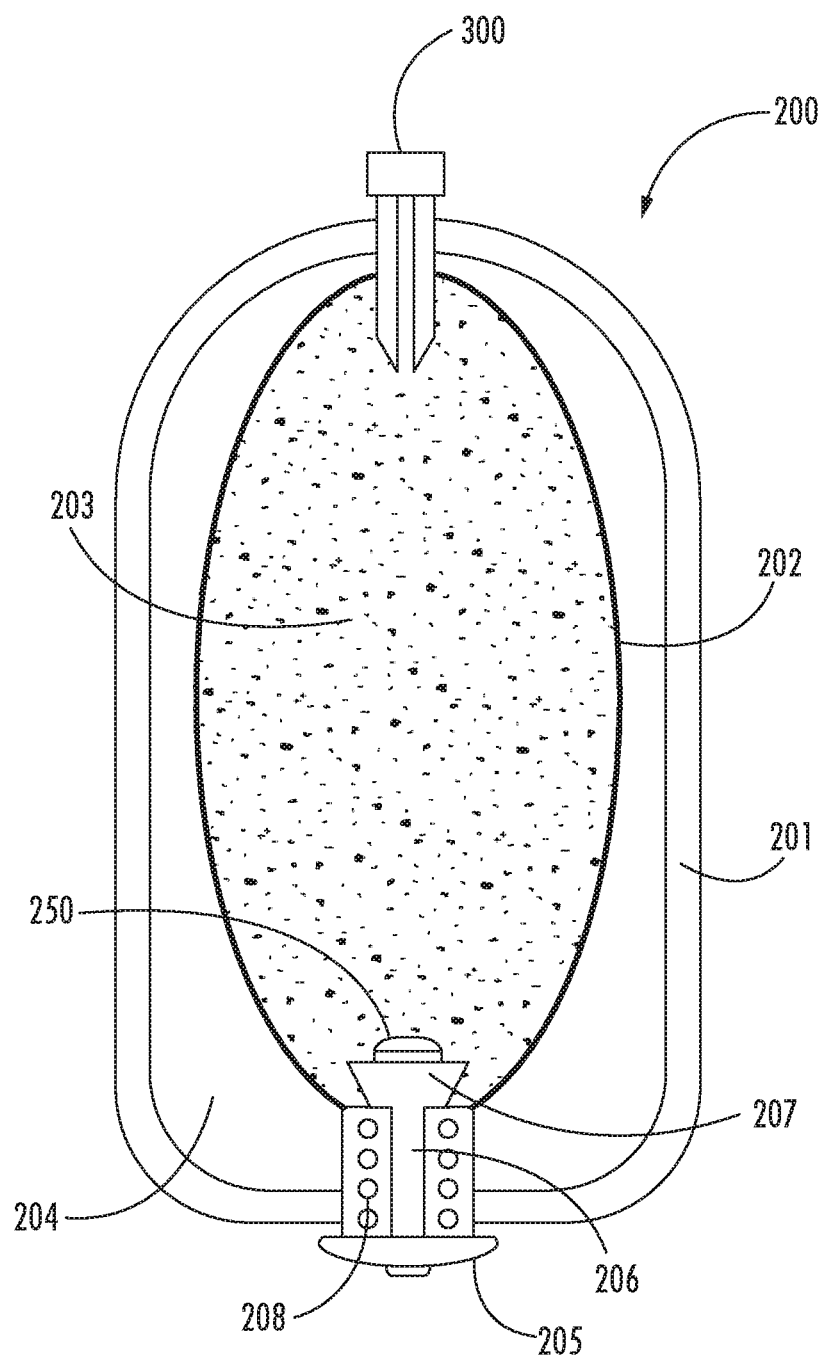
FIG. 4A is a top view diagram of the inside of the replaceable one-time-use reservoir filled with a substance to be dispensed, such as hand sanitizer, with a removable filling nozzle inserted.

FIG. 4A shows a cut-away top diagram of an embodiment of the replaceable one-time-use reservoir 200. Considering FIGS. 1-4(A-C), the replaceable one-time-use reservoir 200 has a flexible bladder 202 and a housing 201 within a rigid perimeter wall 201. The housing 201, rigid perimeter wall 201, and base 7 are each constructed from at least one of steel, zinc, aluminum, acrylonitrile butadience styrene ("ABS"), polycarbonate ("PC"), polypropylene ("PP"), polyamides ("nylon"), polyethylene ("PE"), and polyvinyl chloride ("PVC").

The flexible top surface 2, 102 attaches to the rigid perimeter wall 201 of the housing 201, covering the flexible bladder 202. The flexible top surface 2, 102 is in near proximity with, or touching, the flexible bladder 202. In one embodiment, the flexible top surface 2, 102 is glued or otherwise durably attached to the flexible bladder 202.

The flexible bladder 202 is filled with a substance to be dispensed 203 using a removable feeder tube 300. The substance to be dispensed 203 is typically hand-sanitizer, which is comprised of at least 60% isopropyl alcohol, by volume and aloe vera. The hand sanitizer 203 can be mixed with water to adjust its viscosity. The flexible bladder 202 can be filled to the extent of the rigid perimeter wall 201. As the substance to be dispensed 203 is used, an air gap 204 naturally forms between the flexible bladder 202 and the rigid perimeter wall 201. The flexible bladder 202 is fabricated from an elastic material such as natural rubber, nitrile rubber, butyl rubber, elastomers, or thermoplastic elastomers. The flexible bladder 202 is most appropriately constructed from a synthetic rubber, such as polychloroprene, ethylene-propylene-diene-modified ("EPDM"), styrene-butadiene rubbers ("SBR"), polyisoprene, and acrylonitrile butadiene rubber ("ABR"), inter alia. Prior to filling, the flexible bladder 202 is totally evacuated through the removable feeder tube 300. Once filled with any amount of any substance 203, the flexible bladder 202 has a constant pressure in excess of atmospheric pressure. The replaceable one-time-use reservoir 200 has a one-way valve. The one-way valve is comprised of a plunger 250, an exterior surface 207 shaped like a frustrum of a cone 207, a spring 208, a stem 221, a dispensing channel 206, and a bottom stop 205.

While no pressure is applied by the user 1000 to the flexible top surface 2, the spring 208 keeps the one-way valve closed. When the user 1000 presses the flexible top surface 2, 102, the flexible top surface 2, 102 transfers the force to the flexible bladder 202, creating excess pressure within the flexible bladder 202. The force on the flexible bladder 202 creates more pressure internal to the flexible bladder 202, causing the plunger 250 to overcome the spring force of the spring 208. In this way, the substance 203 in the flexible bladder 202 passes through the one-way valve 266 and is dispensed 4.

Figure 4B:
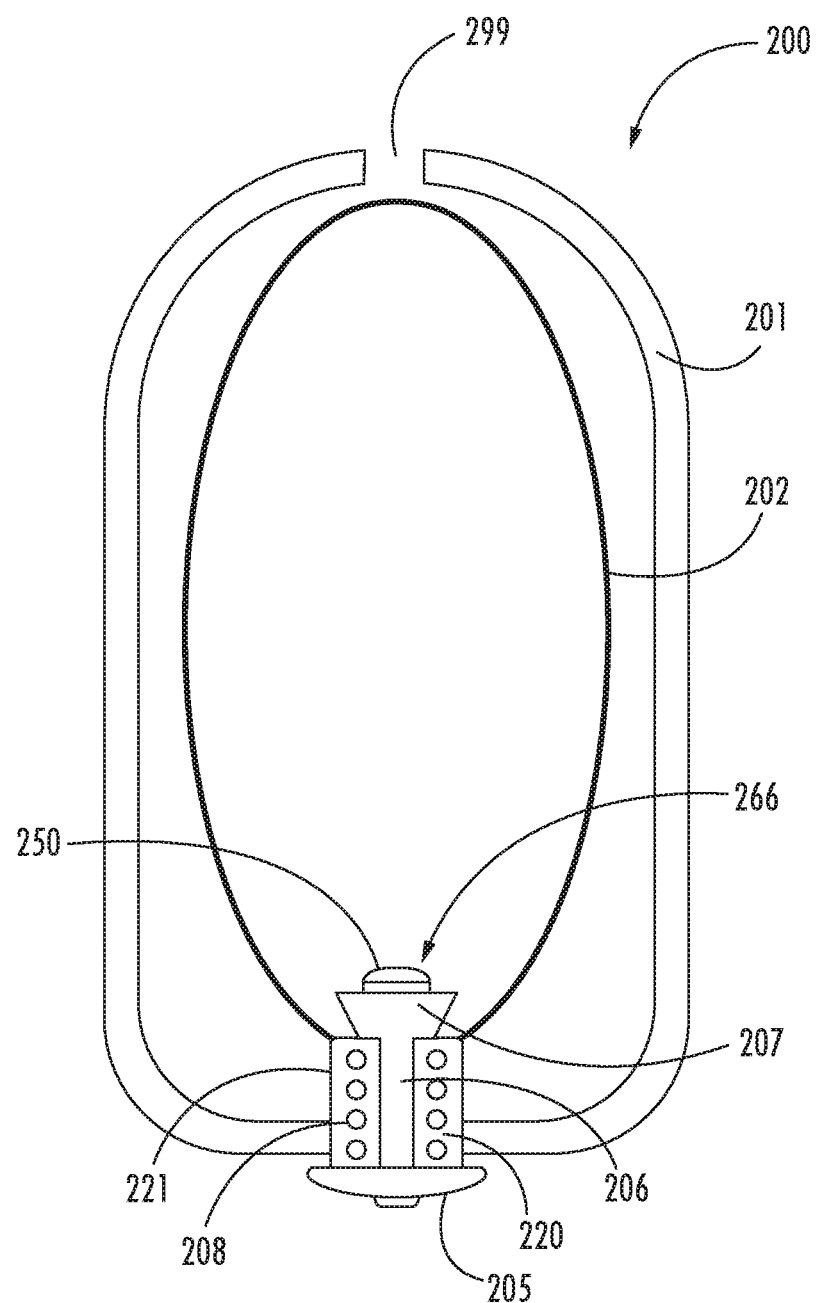
FIG. 4B shows a simplified view of the inside of wearable dispenser with a replaceable one-time-use reservoir, with filling nozzle removed.

FIG. 4B shows the replaceable one-time-use reservoir 200 with the removable feeder tube 300 removed. This creates an opening 299. The flexible bladder 202 is still contained within the rigid perimeter wall 201. The one-way valve 266 is comprised of a plunger 250, an exterior surface 207 shaped like a frustrum of a cone 207, a spring 208 with separation 220 between the spring 208, a stem 221 with an exterior surface 221, a dispensing channel 206 within the stem 221, and a bottom stop 205. The one-way valve 266 allows the substance to be dispensed 203 inside the flexible bladder 202 to be dispensed 4. The one-way valve 266 prevents anything from re-entering the flexible bladder 202 through the one-way valve 266.

Figure 4C:
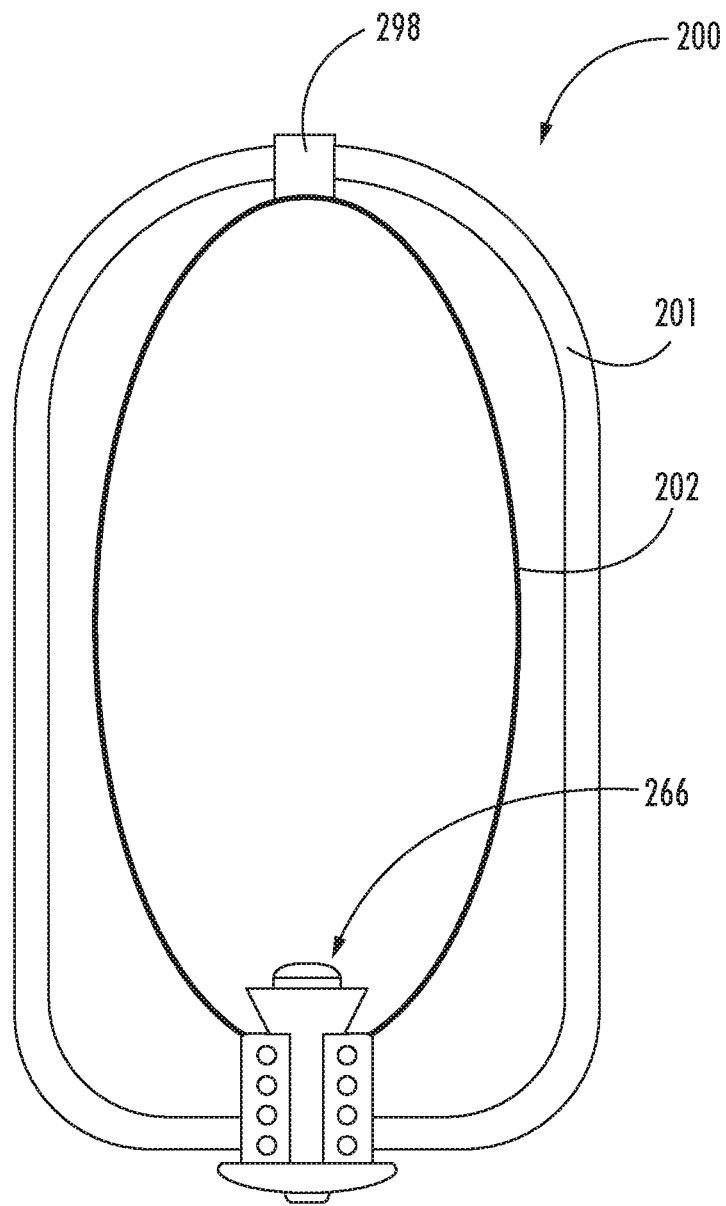
FIG. 4C shows a simplified view of the inside of wearable dispenser with a replaceable one-time-use reservoir with a plug inserted into the hole left by the filling nozzle.

FIG. 4C shows the replaceable one-time-use reservoir 200 with a plug 298 filling the opening 299 left by removing the removable feeder tube 300. The flexible bladder 202 is still contained within the rigid perimeter wall 201. The replaceable one-time-use reservoir 200 has a one-way valve 266.

Figure 5:
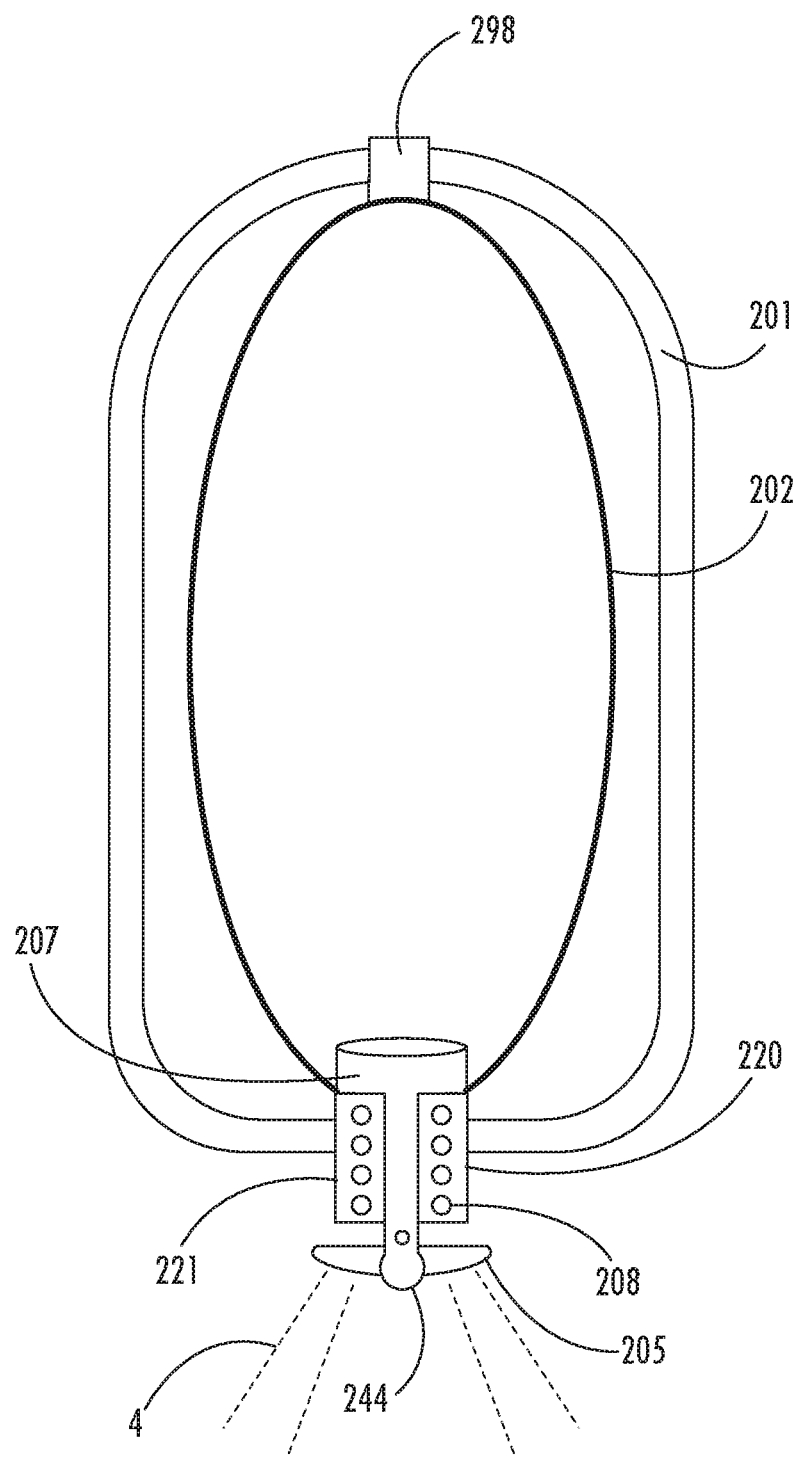
FIG. 5 is a top-view diagram of the inside of the replaceable one-time-use reservoir with a one-way valve activated to dispense.

In FIG. 5, when the top surface of the replaceable one-time-use reservoir 200 is depressed, pressure within the flexible bladder 202 forces the plunger 250 on the one-way valve down, compressing the spring 208 and reducing the space 220 between the spring 208, until the exterior surface 207 can travel no further. The bottom stop 205 is forced away from the one-way valve 266, allowing a substance 4 to come out through a port 244.

Figure 6:
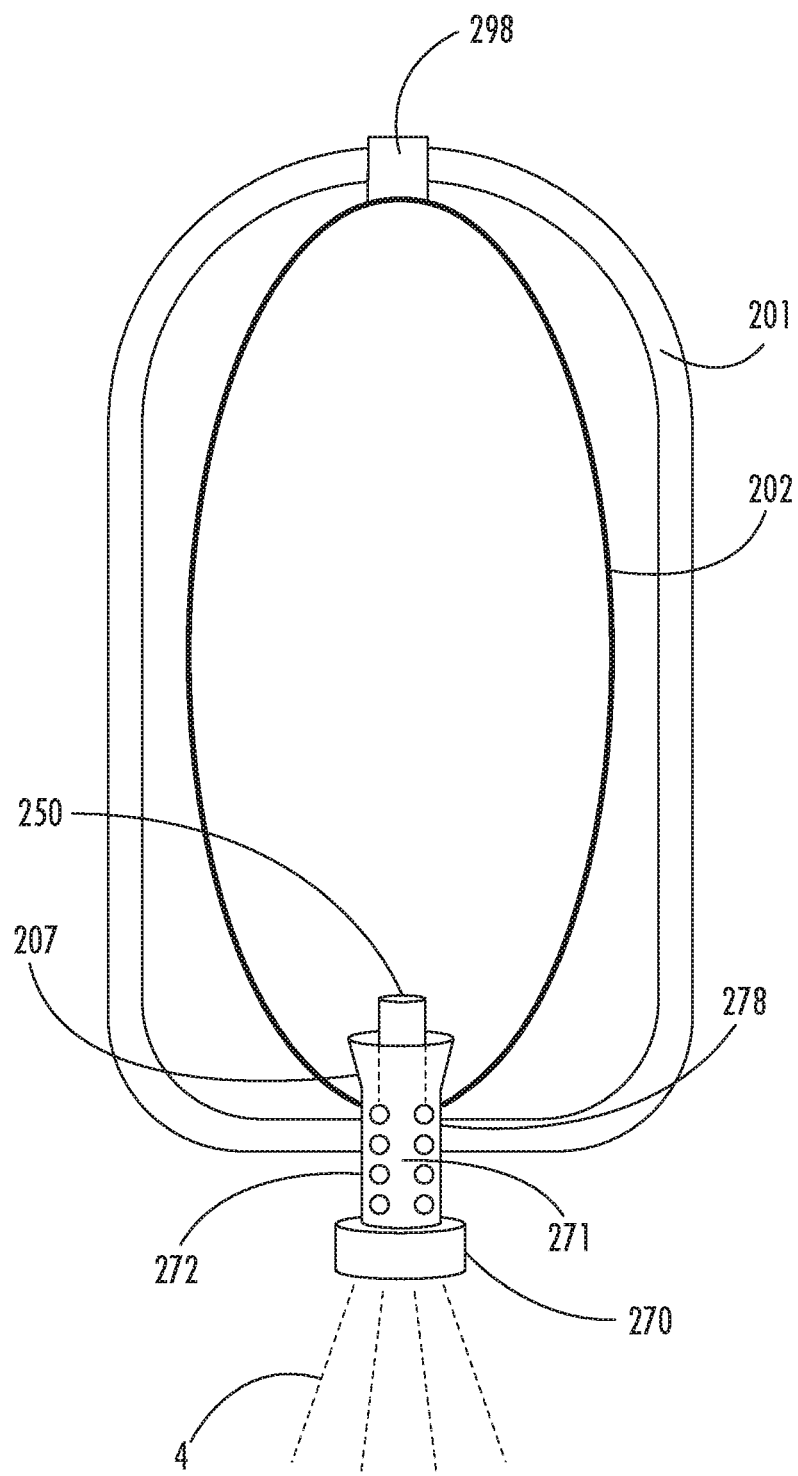
FIG. 6 is a top-view diagram with an alternative embodiment one-way valve with an aerator, used to dispense from the replaceable one-time-use reservoir.

FIG. 6 shows an alternative embodiment further comprising an aerator 270 attached to the bottom of the one-way valve. The aerator 270 is attached to the bottom of the exterior surface 272 of the stem 272. When the top surface of the replaceable one-time-use reservoir 200 is depressed, pressure within the flexible bladder 202 forces the plunger 250 on the one-way valve down, compressing the spring 278 until the substance to be dispensed 4 is forced through the channel 271 and out through the aerator 270. The aerator 270 can be added with substances 4 of a thinner viscosity, so that the result is more of a mist.

Referring to FIGS. 1-6, a replaceable one-time-use reservoir 200 is comprised of a flexible bladder 202, a housing 201 with a rigid perimeter wall 201, a flexible top surface 2, 102 attached to the rigid perimeter wall 201 and covering the flexible bladder 202, a one-way valve 266, and an opening 5. When the replaceable one-time-use reservoir 200 is new, the flexible bladder 202 is filled with a substance to be dispensed 203, such as hand sanitizer. The pressure within the flexible bladder 202 is greater than atmospheric pressure.

The one-way valve 266 is comprised of a plunger 250, a spring 208, a stem 221, 272, and a stop 205. The stem 221, 272 is hollow, creating a dispensing channel 206. The plunger 250 of the valve is inside the flexible bladder 202. When the flexible top surface 2, 102 is not pressed, the one-way valve 266 is in equilibrium. In equilibrium, the spring force of the spring 208 is more than the force created by the pressure on the plunger 250. In equilibrium, the one-way valve 266 is closed. In equilibrium, the stop 205 prevents any of the substance 203 from flowing through the dispensing channel 206.

A user 1000 may use their fingertip 1001 to press the flexible top surface 2, 102. Doing so creates additional pressure within the flexible bladder 202. The combined pressure on the plunger 250 within the flexible bladder 202 is sufficient to compress the springs 208. Once the springs 208 are compressed, the one-way valve 266 allows some of the substance 203 within the flexible bladder 202 to be dispensed 4 through the opening 5. When all of the substance 203 within the flexible bladder 202 has been dispensed 4, the replaceable one-time-use reservoir 200 may be removed and replaced with a new replaceable one-time-use reservoir 200.

Embodiments may be described above with reference to functions or acts, which comprise methods. The functions/acts noted above may occur out of the order as shown or described. For example, two functions/acts shown or described in succession may in fact be executed substantially concurrently or the functions/acts may sometimes be executed in the reverse order, depending upon the functionality/acts involved. While certain embodiments have been described, other embodiments may exist. Further, the disclosed methods' functions/acts may be modified in any manner, including by reordering functions/acts and/or inserting or deleting functions/acts, without departing from the spirit of the claimed subject matter.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A wearable dispenser with a replaceable one-time-use reservoir device comprising,
   a wrist-band allowing the wearable dispenser to be worn by a user;
   a base connected to the wrist-band; and
   a replaceable one-time-use reservoir comprising
      a substance to be dispensed,
      a flexible bladder for holding the substance to be dispensed,
      a housing with a rigid perimeter wall,
      a flexible top surface attached to the rigid perimeter wall and covering the flexible bladder,
      a one-way valve,
      an opening, and
      a plug
   wherein, prior to use, the flexible bladder is totally evacuated through a removable feeder tube, filled with the substance to be dispensed, and then plugged with the plug;
   wherein, once filled with any amount of the substance to be dispensed, the flexible bladder is under a constant pressure in excess of atmospheric pressure;
   wherein the replaceable one-time-use reservoir is attached to the base;
   wherein pressing the flexible top surface will cause the one-way valve to open, dispensing the substance to be dispensed through the opening; and
   wherein the one-way valve is comprised of a spring having a spring force, a hollow stem with a dispensing channel, a plunger, and a stop.

2. The wearable dispenser with replaceable one-time-use reservoir device of claim 1, wherein a user may empty the flexible bladder of the substance by repeatedly pressing the flexible top surface.

3. The wearable dispenser with replaceable one-time-use reservoir device of claim 2, wherein the empty replaceable one-time-use reservoir may be detached from the base.

4. The wearable dispenser with replaceable one-time-use reservoir device of claim 3, wherein a new replaceable one-time-use reservoir, filled with the substance, may be attached to the base.

5. The wearable dispenser with a replaceable one-time-use reservoir device of claim 4, wherein the substance is hand sanitizer.

6. The wearable dispenser with replaceable one-time-use reservoir device of claim 5, wherein the hand sanitizer is comprised of at least 60% alcohol and aloe vera.

7. The wearable dispenser with a replaceable one-time-use reservoir device of claim 6, further comprising an aerator attached to the one-way valve.

8. The wearable dispenser with replaceable one-time-use reservoir device of claim 7, wherein the hand sanitizer is further comprised of water.

9. The wearable dispenser with a replaceable one-time-use reservoir device of claim 1, wherein the plunger is internal to the flexible bladder.

10. The wearable dispenser with a replaceable one-time-use reservoir device of claim 9, wherein the one-way valve does not allow anything to enter the flexible bladder.

11. The wearable dispenser with a replaceable one-time-use reservoir device of claim 10, wherein, when the flexible top surface is not being pressed, the one-way valve is in equilibrium, and the spring force of the spring is greater than the force created by pressure on the plunger, allowing the stop to prevent any substance from flowing through the dispensing channel.

12. The wearable dispenser with a replaceable one-time-use reservoir device of claim 11, wherein pressing the flexible top surface creates sufficient pressure within the flexible bladder so that the force created by pressure on the plunger overcomes the spring force of the spring, allowing the substance to flow through the dispensing channel.

13. The wearable dispenser with a replaceable one-time-use reservoir device of claim 12, wherein the flexible bladder is fabricated from at least one of natural rubber, nitrile rubber, butyl rubber, an elastomer, and a thermoplastic elastomer.

14. The wearable dispenser with a replaceable one-time-use reservoir device of claim 12, wherein the flexible bladder is fabricated from at least one of polychloroprene, ethylene-propylene-diene-modified ("EPDM"), styrene-butadiene rubbers ("SBR"), polyisoprene, polyvinyl chloride ("PVC"), and acrylonitrile butadiene rubber ("ABR").

15. The wearable dispenser with a replaceable one-time-use reservoir device of claim 14, wherein the housing is fabricated from at least one of steel, zinc, aluminum, acrylonitrile butadience styrene ("ABS"), polycarbonate ("PC"), polypropylene ("PP"), polyamides ("nylon"), polyethylene ("PE"), and polyvinyl chloride ("PVC").

16. The wearable dispenser with a replaceable one-time-use reservoir device of claim 15, wherein the base is fabricated from at least one of steel, zinc, aluminum, ABS, PC, PP, nylon, PE, and PVC.

\* \* \* \* \*